United States Patent
Igarashi

(10) Patent No.: US 6,307,083 B1
(45) Date of Patent: Oct. 23, 2001

(54) SPECIFIC SILANE COMPOUNDS, METHOD OF SYNTHESIZING THEM, LUMINESCENT DEVICE MATERIALS COMPRISING THEM, AND LUMINESCENT DEVICES CONTAINING SUCH MATERIALS

(75) Inventor: Tatsuya Igarashi, Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/542,287

(22) Filed: Apr. 4, 2000

(30) Foreign Application Priority Data

Apr. 7, 1999 (JP) .................................................. 11-100498

(51) Int. Cl.$^7$ .............................. C07F 7/08; H05B 33/00; H05B 33/12; H05B 33/14
(52) U.S. Cl. .......................... 556/489; 556/430; 556/431; 428/690; 428/212; 428/917; 313/504; 313/506; 549/6; 549/214; 548/110; 544/229; 546/14
(58) Field of Search ...................................... 556/430, 431, 556/489; 428/690, 212, 917; 313/504, 506; 549/4, 214; 546/14; 548/110; 544/229

(56) References Cited

U.S. PATENT DOCUMENTS

| | | | |
|---|---|---|---|
| 5,432,014 | * | 7/1995 | Sano et al. ............................ 428/690 |
| 5,449,564 | * | 9/1995 | Nishio et al. .......................... 428/690 |
| 5,529,853 | * | 6/1996 | Hamada et al. ....................... 428/690 |
| 5,601,903 | * | 2/1997 | Fujii et al. ......................... 428/690 X |
| 5,674,597 | * | 10/1997 | Fujii et al. ......................... 428/690 X |
| 5,792,557 | * | 8/1998 | Nakaya et al. ..................... 428/690 X |
| 5,830,972 | * | 11/1998 | Ueda et al. ........................ 556/430 X |
| 5,837,391 | * | 11/1998 | Utsugi .................................. 428/690 |
| 5,858,564 | * | 1/1999 | Tamura et al. ........................ 428/690 |
| 5,861,469 | * | 1/1999 | Auner et al. ...................... 556/431 X |
| 5,965,684 | * | 10/1999 | Auner et al. ...................... 556/431 X |
| 6,066,712 | * | 5/2000 | Yeda et al. ...................... 556/431 UX |
| 6,165,383 | * | 12/2000 | Chou ................................. 556/431 X |
| 6,232,001 | * | 5/2001 | Igarashi ................................ 428/690 |

FOREIGN PATENT DOCUMENTS

A-11-3781 1/1999 (JP) .

OTHER PUBLICATIONS

Synthetic Metals, 91, pp. 297–299 (1997).
Japanese Patent Office—Patent Abstracts of Japan Publication No. 11003781, 1999.

\* cited by examiner

Primary Examiner—Paul F. Shaver
(74) Attorney, Agent, or Firm—Sughrue, Mion, Zinn, Macpeak & Seas, PLLC

(57) ABSTRACT

Silane compounds represented by formula (1), a synthesis method thereof, luminescent device materials comprising such silane compounds, and luminescent devices containing such materials:

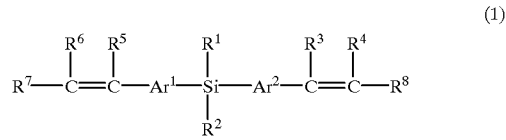

(1)

wherein each of $R^1$ and $R^2$ groups represents an aryl group containing no alkenyl substituent, or a heteroaryl group containing no alkenyl substituent; each of $R^3$, $R^4$, $R^5$ and $R^6$ groups represents a hydrogen atom or a substituent group; each of $R^7$ and $R^8$ groups represents an aryl group or a heteroaryl group; and each of $Ar^1$ and $Ar^2$ groups represents an arylene group or a heteroarylene group; provided that the compound represented by the formula (1) takes neither polymeric nor oligomeric form and the case is excluded therefrom wherein all or three of $R^1$ $R^2$, $Ar^1$ and $Ar^2$ groups have heteroaryl structures.

4 Claims, No Drawings

SPECIFIC SILANE COMPOUNDS, METHOD OF SYNTHESIZING THEM, LUMINESCENT DEVICE MATERIALS COMPRISING THEM, AND LUMINESCENT DEVICES CONTAINING SUCH MATERIALS

FIELD OF THE INVENTION

The present invention relates to silane compounds, a method of synthesizing them, luminescent device materials comprising silane compounds, and luminescent devices containing such materials.

BACKGROUND OF THE INVENTION

Nowadays various types of display devices using organic fluorescent materials (organic luminescent devices) are actively researched and developed. Of these devices, much attention is focused on organic electroluminescent (EL) devices. This is because organic EL devices are promising display devices capable of emitting light of high luminance under a low applied voltage. For instance, the EL devices of a type which comprises organic thin layers formed by evaporating organic compounds are known (*Applied Physics Letters*, vol. 51, p. 913 (1987)). More specifically, the organic EL devices of such a type have a laminated structure made up of an electron transfer material and a hole transfer material, and their luminous characteristics show substantial improvements over those of conventional devices of single-layer type.

With the reports printed in the journal described above, the study and development of organic EL devices have been made energetically. And developments of electron transfer materials and hole transfer materials have been attempted with the intention of enhancing luminous efficiency. As to the development of electron transfer materials, however, no compounds superior in properties to tris(8-hydroxyquinolinato)aluminum (usually abbreviated as "Alq") have yet been found. Such being the case, it has been desired to develop compounds capable of surpassing Alq in properties. In addition, Alq fluoresces a green color, so that it has no suitability as an electron transfer material for blue luminescent devices Therefore, it has been desired to find out electron transfer materials suitable for blue luminescent devices.

Also, the application of organic EL devices to full color display has been lively examined in recent years. In order to develop a high-performance full color display, it is necessary to heighten the color purity of each of blue luminescence, green luminescence and red luminescence. However, the luminescence of high color purity is difficult to obtain. For instance, the distyrylarylene compounds (DPVBi) described in a book, entitled *Yuki EL Soshi to sono Kogyoka Saizensen* (which means "Organic EL devices and the forefront of their industialization"), page 38, published by N.T.S. Co., and $Zn(OXZ)_2$ (benzene ring-condensed nitrogen-containing heterocyclic compounds) described in the book, supra, page 40, and JP-A-7-133483 (the term "JP-A" as used herein means an "unexamined published Japanese patent application") are blue luminescent materials which have undergone extensive examinations, but they can merely provide blue luminescence of low color purity. Therefore, there is plenty of room for improvement.

Another important characteristic that is required for organic EL device materials is durability. In particular, the amorphous film stability constitutes an important factor in the enhancement of durability. Therefore, it has been expected to develop compounds usable as organic EL device materials and capable of forming highly stable amorphous films. For instance, N,N'-diphenyl-N,N'-di(m-tolyl)benzidine (TPD) is an extensively utilized hole transfer material and has high hole transfer capacity. Although the TPD evaporated film can be in a uniform amorphous state for a short while after the evaporation was finished, cases occurs in which the evaporated film crystallizes after a lapse of several hours. In such cases, the durability of EL devices is greatly lowered.

SUMMARY OF THE INVENTION

Objects of the present invention are to develop an organic luminescent device material which can ensure high luminous efficiency and high durability in the organic luminescent device, and to provide a luminescent device comprising such a material.

The aforementioned objects are attained in accordance with the following Embodiments (1) to (4).

(1) A compound represented by the following formula (1):

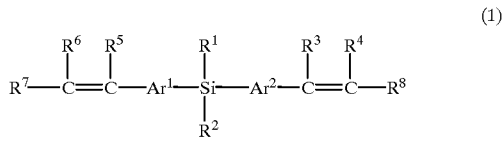

wherein each of $R^1$ and $R^2$ groups represents an aryl group containing no alkenyl substituent or a heteroaryl group containing no alkenyl substituent; each of $R^3$, $R^4$, $R^5$ and $R^6$ groups represents a hydrogen atom or a substituent group; each of $R^7$ and $R^8$ groups represents an aryl group or a heteroaryl group; and each of $Ar^1$ and $Ar^2$ groups represents an arylene group or a heteroarylene group; provided that the compound represented by the formula (1) takes neither polymeric nor oligomeric form and the case is excluded therefrom wherein all or three of $R^1$, $R^2$, $Ar^1$ and $Ar^2$ groups have heteroaryl structures.

(2) A luminescent device material, comprising a compound represented by the formula (1) defined in Embodiment (1).

(3) A luminescent device, containing at least one compound represented by the formula (1) defined in Embodiment (1).

(4) A method of synthesizing a compound represented by the formula (1) defined in Embodiment (1), comprising a step of reacting an alkenyl compound with the halide or trifluoromethanesulfonate derivative in the presence of a palladium catalyst to form the C—C bond.

DETAILED DESCRIPTION OF THE INVENTION

The compounds represented by formula (1) of the present invention are described below in detail.

$R^1$ and $R^2$ each represents an aryl group having no alkenyl substituent (containing preferably 6 to 30, more preferably 6 to 20, particularly preferably 6 to 12, carbon atoms, with examples including phenyl, p-methylphenyl and naphthyl groups) or a heteroaryl group having no alkenyl substituent (containing preferably 1 to 50, more preferably 1 to 30, particularly preferably 2 to 12, carbon atoms in addition to any of oxygen, sulfur and nitrogen atoms, with examples including imidazolyl, pyridyl, furyl, thienyl, piperidyl, benzoxazolyl and triazolyl groups). The aryl or heteroaryl group represented by $R^1$ and $R^2$ each may be substituted by any of the substituent groups represented by $R^3$, which are described below, as long as an alkenyl group is excluded therefrom.

It is desirable for $R^1$ and $R^2$ each to be an unsubstituted aryl group or an unsubstituted heteroaryl group, further preferably an unsubstituted aryl group, particularly preferably an unsubstituted phenyl group.

Each of $R^3$, $R^4$, $R^5$ and $R^6$ groups represents a hydrogen atom or a substituent group. Examples of such a substituent group include an alkyl group (containing preferably 1 to 30, more preferably 1 to 12, further preferably 1 to 6, carbon atoms, with examples including methyl, t-butyl and hexyl groups), an alkenyl group (containing preferably 2 to 30, more preferably 2 to 12, further preferably 2 to 6, carbon atoms, such as a propenyl group), an alkynyl group (containing preferably 2 to 30, more preferably 2 to 12, further preferably 2 to 6, carbon atoms, such as an ethynyl group), an aryl group (containing preferably 6 to 40, more preferably 6 to 20, further preferably 6 to 12, carbon atoms, with examples including phenyl, naphthyl and anthryl groups), a heteroaryl group (containing preferably 1 to 40, more preferably 2 to 20, further preferably 3 to 12, carbon atoms in addition to any of oxygen, sulfur and nitrogen atoms, with examples including pyridyl, thienyl and carbazolyl groups), an alkoxy group (containing preferably 1 to 30, more preferably 1 to 12, further preferably 1 to 6, carbon atoms, such as a methoxy group or an isopropoxy group), an aryloxy group (containing preferably 6 to 40, more preferably 6 to 20, further preferably 6 to 12, carbon atoms, with examples including phenoxy, naphthoxy and pyrenyloxy groups), a halogen atom (such as chlorine, bromine or fluorine atom), an aliphatic heterocyclic group (containing preferably 1 to 40, more preferably 2 to 20, further preferably 3 to 12, carbon atoms in addition to any of oxygen, sulfur and nitrogen atoms, such as s piperidyl group or a morpholino group), and a cyano group. These substituent groups each may further have a substituent group.

It is desirable for $R^3$, $R^4$, $R^5$ and $R^6$ each to be a hydrogen atom, an alkyl group, an aryl group, a heteroacryl group or a cyano group, more preferably a hydrogen atom, an alkyl group or an aryl group, further preferably a hydrogen atom or an alkyl group, particularly preferably a hydrogen atom.

Each of $R^7$ and $R^8$ groups represents an aryl group or a heteroaryl group. It is desirable for $R^7$ and $R^8$ each to be an aryl group, more preferably a naphthyl group, a phenyl group or an anthryl group, further preferably a phenyl group.

Each of $Ar^1$ and $Ar^2$ groups represents an arylene group (containing preferably 6 to 40, more preferably 6 to 30, further preferably 6 to 12, carbon atoms, with examples including phenylene, naphthylene, anthrylene and pyrenylene groups) or a heteroarylene group (containing preferably 1 to 50, more preferably 1 to 30, particularly preferably 2 to 12, carbon atoms in addition to any of oxygen, sulfur and nitrogen atoms, with examples including imidazolylene, pyridylene, pyrazinylene, furylene, benzazolylene (including benzoxazolylene, benzimidazolylene and benzothiazolylene, preferably benzoxazolylene and benzimidazolylene, more preferably benzimidazolylene) and triazolylene groups).

It is desirable for $Ar^1$ and $Ar^2$ each to be an arylene group or a nitrogen-containing heteroarylene group, more preferably an arylene group, further preferably a phenylene group, particularly preferably an unsubstituted p-phenylene group.

The compounds of the present invention assume neither polymeric nor oligomeric form, and do not include the cases where all or three of the $R^1$, $R^2$, $Ar^1$ and $Ar^2$ groups have heteroaryl structures.

The appropriate molecular weight of the compounds of the present invention each is from 300 to 3,000, preferably from 500 to 2,000, more preferably from 500 to 1,500, particularly preferably 700 to 1,200. Further, it is desirable for the compounds of the present invention to contain one silicon atom per molecule.

Of the compounds of the present invention, the compounds represented by the following formula (2) are preferred over the others:

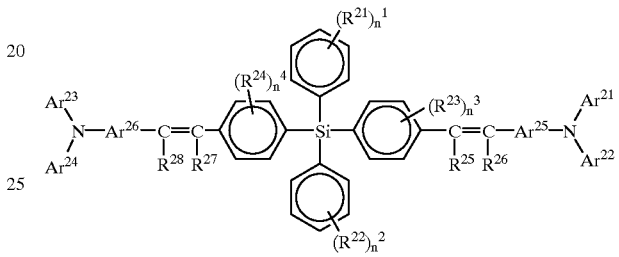

(2)

wherein each of $R^{21}$ and $R^{22}$ groups represents a substituent group other than an alkenyl group; each of $R^{23}$ and $R^{24}$ groups represents a substitutent group; $n^1$ and $n^2$ are each an integer of from 0 to 5; $n^3$ and $n^4$ are each an integer of from 0 to 4. When any of $n^1$, $n^2$, $n^3$ and $n^4$ is at least 2, the corresponding $R^{21}$, $R^{22}$, $R^{23}$ or $R^{24}$ groups may be the same or different. It is desirable for the $R^{21}$, $R^{22}$, $R^{23}$ and $R^{24}$ groups each to be an alkyl group, an aryl group, a heteroaryl group, an alkoxy group, an aryloxy group, an alkylthio group, an arylthio group, a substituted or unsubstituted amino group or a cyano group, more preferably an alkyl group, an aryl group or a heteroaryl group, further preferably an alkyl group, particularly preferably a methyl group.

It is desirable for $n^1$, $n^2$, $n^3$ and $n^4$ each to be 0, 1 or 2, more preferably 0 or 1, further preferably 0.

Each of $R^{25}$, $R^{26}$, $R^{27}$ and $R^{28}$ groups has the same meaning as the foregoing $R^3$. $Ar^{25}$ and $Ar^{26}$ each represents an arylene group or a heteroarylene group, and the desirable scope thereof is the same as that of the foregoing $Ar^1$.

Each of $Ar^{21}$, $Ar^{22}$, $Ar^{23}$ and $Ar^{26}$ groups represents an aryl group or a heteroaryl group. Further, it is all right to combine $Ar^{21}$, $Ar^{22}$ and $AR^{25}$ into a nitrogen-containing hetero ring, and also combine $Ar^{23}$, $Ar^{24}$ and $Ar^{26}$ into a nitrogen-containing hetero ring. However, it is desirable for $Ar^{21}$, $Ar^{22}$, $Ar^{23}$ and $Ar^{24}$ each to be an aryl group, more preferably a phenyl or naphthyl group, further preferably an unsubstituted phenyl group, an alkyl-substituted phenyl group or a naphthyl group, particularly preferably an unsubstituted phenyl group.

Suitable examples of a compound according to the present invention are illustrated below, but it should be understood that these examples are not to be construed as limiting the scope of the invention in any way.

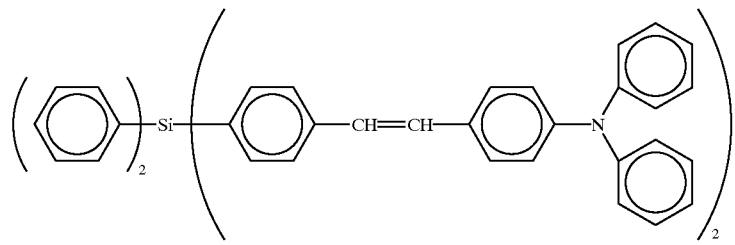
(1-1)
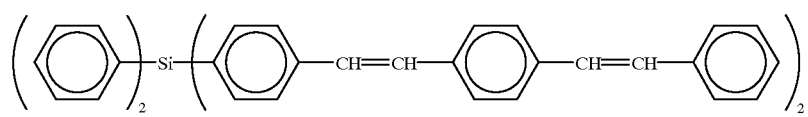
(1-2)
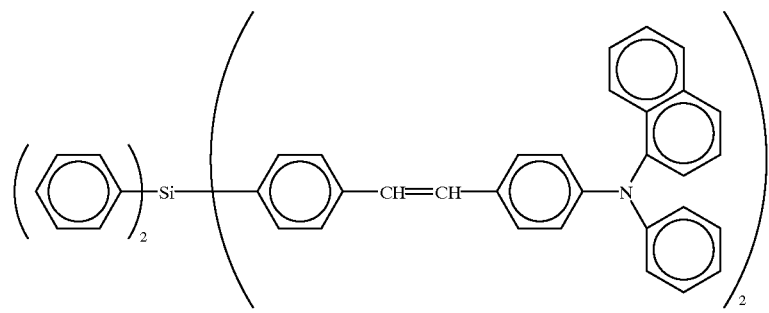
(1-3)
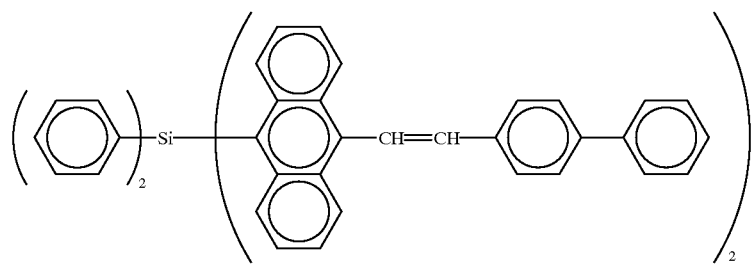
(1-4)
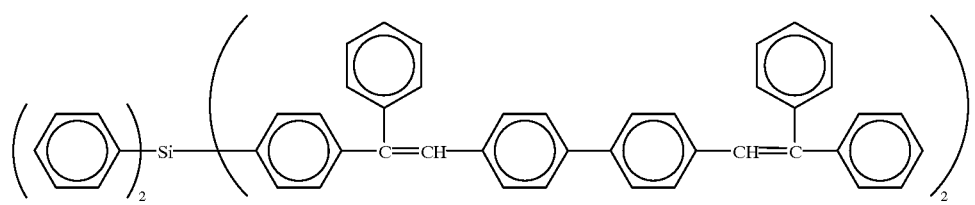
(1-5)
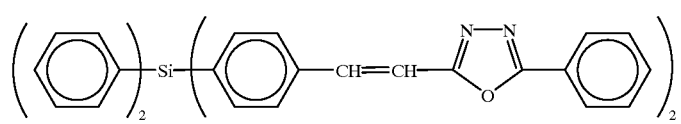
(1-6)
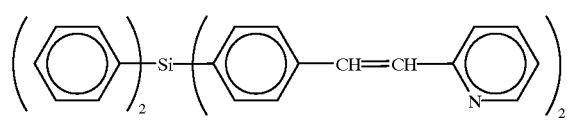
(1-7)

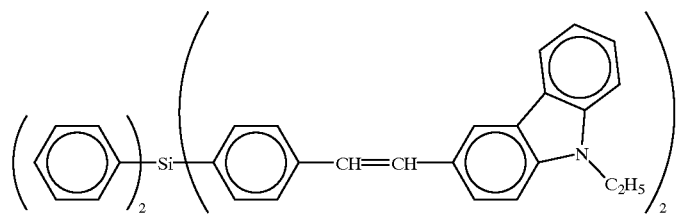
(1-8)
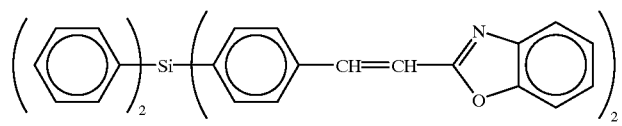
(1-9)
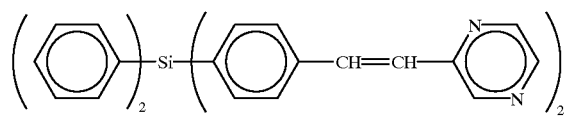
(1-10)
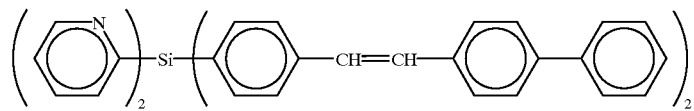
(1-11)
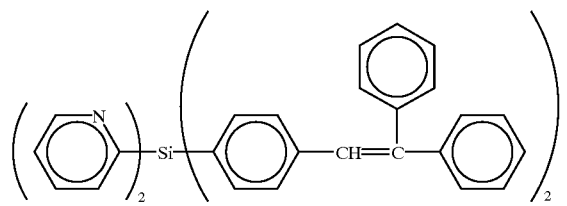
(1-12)
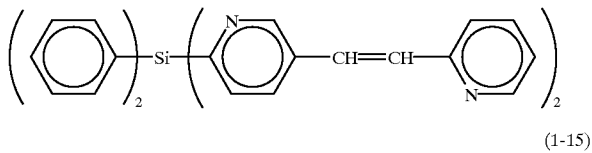
(1-13)
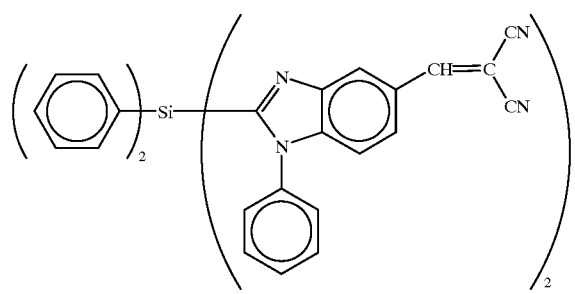
(1-14)
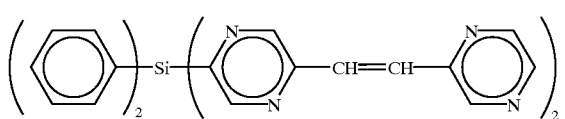
(1-15)
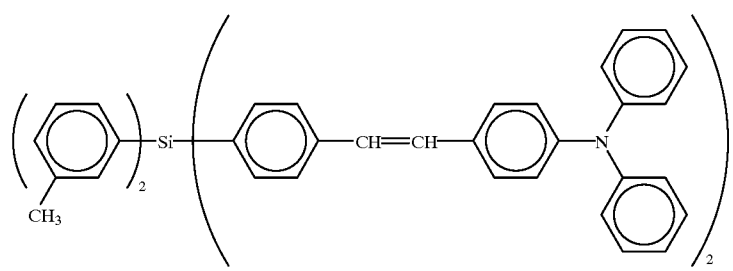
(1-16)

-continued
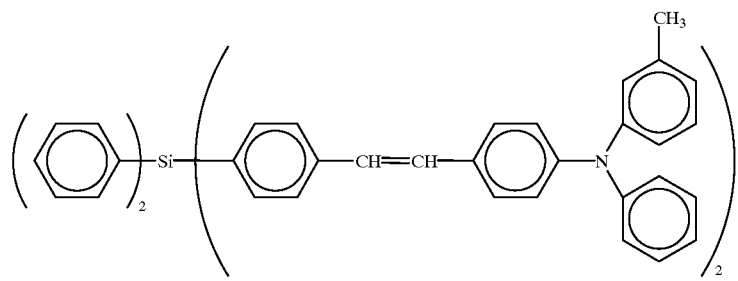
(1-17)
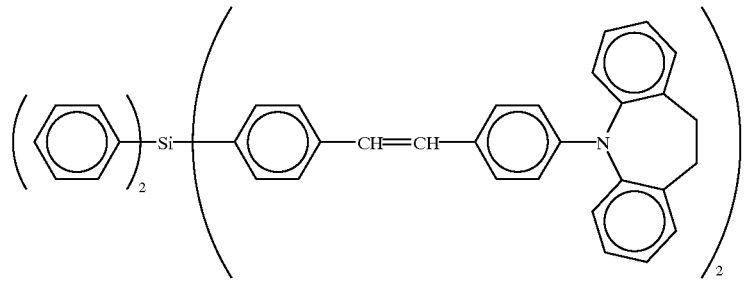
(1-18)
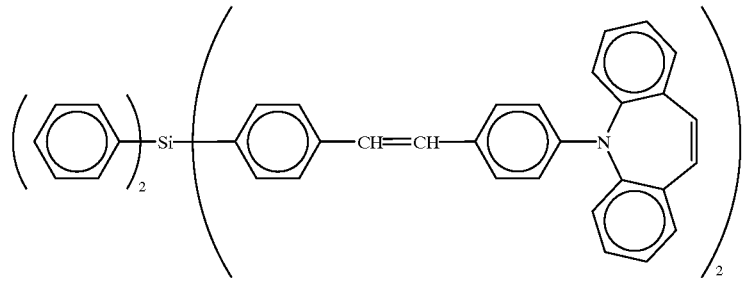
(1-19)
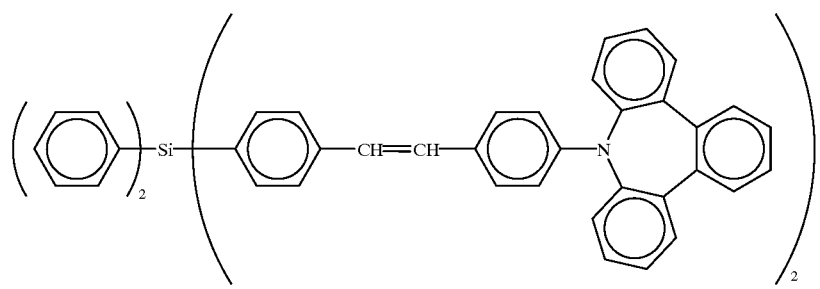
(1-20)
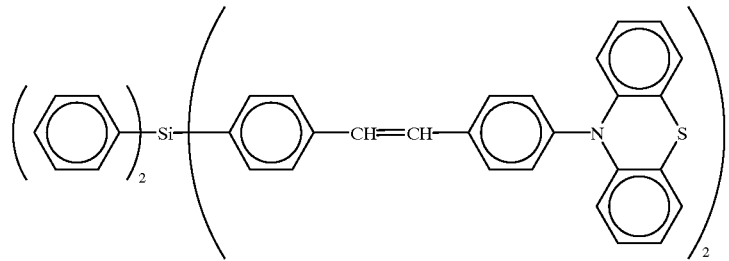
(1-21)

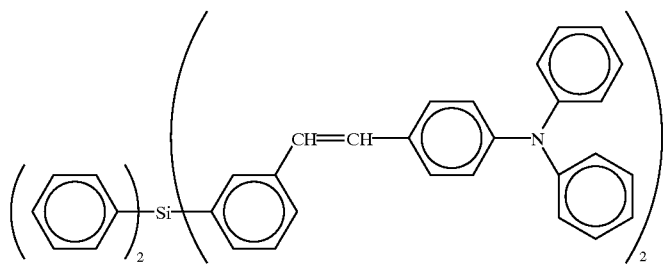

(1-22)

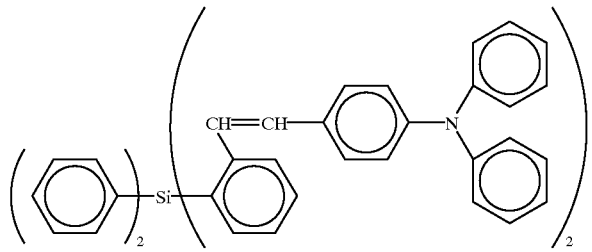

(1-23)

Methods of synthesizing the compounds of the present invention are illustrated below. From the viewpoint of their easy syntheses, it is undesirable that the compounds of the present invention have a spiro-structure containing a silicon atom as the spiro-atom.

The compounds of the present invention can be synthesized using various known methods. For instance, they can be synthesized utilizing the reaction between lithioaryl derivatives and halogenated silicon compounds. Further, the bond between $Ar^1$ and alkenyl group and the bond between $Ar^2$ and alkenyl group can be formed by allowing the —$Ar^1$—X and —$Ar^2$—X (X=F, Cl, Br, I or —$OSO_2CF_3$, preferably Br or I) moieties of a silane derivative to react with $CHR^5$=$CR^6R^7$ and $CHR^3$=$CR^4R^8$ respectively in the presence of a metallic catalyst.

There is no particular restriction on the metallic catalyst used in the foregoing process, but palladium compounds are used to advantage. The palladium compounds usable as the catalyst have no particular limitations on their valence number and ligands, but examples thereof include palladium tetrakistriphenylphosphine, palladium carbon, palladium dichloride dppf (wherein "dppf" stands for 1,1-bis-diphenylphosphinoferrocene), and palladium acetate.

Then, the luminescent devices comprising compounds according to the present invention are illustrated below.

It does not matter what system, operation method and utilization form are applied to the luminescent devices of the present invention as long as the organic luminescent devices of the present invention utilize the silane compounds of the present invention. However, it is desirable for the luminescent devices of the present invention to be luminescent devices utilizing luminescence from the compounds of the present invention or those using the compounds of the present invention as electric charge transfer materials. One of the representatives of organic luminescent devices is an organic electroluminescent (EL) device.

The organic layers of a luminescent device comprising any of the silane compounds of the present invention have no particular restrictions as to the formation method. Various methods, such as a resistance heating-utilized vapor deposition method, an electron-beam method, a sputtering method, a molecular lamination method and a coating method can be adopted. In particular, the resistance heating-utilized vapor deposition method and the coating method are advantageous methods from the viewpoint of the production efficiency, and the resistance heating-utilized vapor deposition method is more preferable.

Every luminescent device of the present invention is a device having a luminescent layer or at least two thin layers of organic compounds, including a luminescent layer, between a pair of electrodes, an anode and a cathode. The thin layers which the device may have in addition to the luminescent layer are, e.g., a hole injection layer, a hole transfer layer, an electron injection layer, an electron transfer layer and a protective layer. The aforementioned layers each may have another function also. For forming each layer, various materials can be employed.

The anode supplies holes to a hole injection layer, a hole transfer layer and a luminescent layer. As an anode material can be used a metal, an alloy, a metal oxide, an electrically conductive material or a mixture of two or more thereof, preferably a material having a work function of at least 4 eV. Examples of such a material include conductive metal oxides, such as tin oxide, zinc oxide, indium oxide and indium tin oxide (ITO), metals such as gold, silver, chromium and nickel, mixtures or laminates of those metals and conductive metal oxides, inorganic conductive materials such as copper iodide and copper sulfide, organic conductive materials such as polyaniline, polythiophene and polypyrrole, and laminates of those materials and ITO. Of the materials described above, the conductive metal oxides are preferred over the others. In particular, ITO is advantageous from the viewpoints of productivity, conductivity and transparency. The suitable thickness of the anode, though can-be selected depending on the anode material, is generally from 10 nm to 5 $\mu$m, more preferably 50 nm to 1 $\mu$m, further preferably 100 nm to 500 nm.

The anode has on a soda lime glass, alkali-free glass or transparent resin substrate an anode material formed into a layer. In a case of using a glass substrate, alkali-free glass is preferred from the viewpoint of reduction in ions eluted from the glass. When soda lime glass is used as the substrate, it is desirable that the barrier coat, such as silica, be provided on the glass. The thickness of the substrate has no particular limitation as long as the substrate can ensure mechanical strength for the anode. For instance, the suitable thickness of a glass substrate is at least 0.2 mm, preferably at least 0.7 mm.

The methods suitable for making the anode vary with the material used. In the case of ITO, for example, the film formation can be carried out using an electron-beam method, a sputtering method, a resistance heating-utilized vapor deposition method, a chemical reaction method (e.g., sol-gel method) or the method of coating a dispersion of indium tin oxide.

Washing and other treatments for the anode enable the device to get a reduction in operation potential and have an improvement in luminous efficiency. In the case of an anode using ITO, it is effective for the anode to receive UV-ozone treatment or plasma treatment.

The cathode supplies electrons to an electron injection layer, an electron transfer layer and a luminescent layer. In selecting the cathode, the adhesiveness to the electron injection, electron transfer or luminescent layer adjacent to the cathode, the ionization potential and the stability are taken into consideration. As a cathode material can be employed a metal, an alloy, a metal halide, a metal oxide, an electrically conductive material or a mixture of two or more thereof. Examples of those materials include alkali metals (e.g., Li, Na, K) and the fluorides thereof, alkaline earth metals (e.g., Mg, Ca) and the fluorides thereof, gold, silver, lead, aluminum, Na—K alloy or a mixture with the other metallic element, Li—Al alloy or a mixture with the other metallic element, Mg—Ag alloy or a mixture with the other metallic element, and rare earth metals (e.g., In, Yb). Of these materials, the materials having a work function of at most 4 eV are preferred over the others. In particular, aluminum, Li—Al alloy or a mixture with the other metallic element, and Mg—Ag alloy or a mixture with the other metallic element are used to advantage. The cathode structure may be a single-layer of the compound or a mixture thereof as described above or a lamination comprised of the compounds or mixtures thereof as described above. The suitable thickness of the cathode, though can be selected depending on the cathode material, is generally from 10 nm to 5 $\mu$m, more preferably 50 nm to 1 $\mu$m, further preferably 100 nm to 1 $\mu$m.

In forming the cathode, various known methods, such as an electron-beam method, a sputtering method, a resistance heating-utilized vapor deposition method and a coating method, can be adopted. The metals as described above may be evaporated independently, or two or more thereof may be evaporated simultaneously. Further, it is possible to evaporate a plurality of metals at the same time to form an alloy electrode, or to evaporate the previously prepared alloy. It is advantageous to the luminescent device that both anode and cathode have low sheet resistance, specifically not higher than several hundreds $\Omega/\square$.

The material for a luminescent layer may be any of materials capable of forming a layer which can function so as to receive both hole injection from the anode, the hole injection layer or the hole transfer layer and electron injection from the cathode, the electron injection layer or the electron transfer layer when the electric field is applied thereto, permit the charges injected therein to move and enable the emission of light by providing a place for recombining the holes and the electrons. In a preferred embodiment of the present invention, the luminescent layer contains the silane compound(s) of the present invention. However, other materials hitherto known to be luminescent may be employed for the luminescent layer. Examples of such a luminescent material include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne derivatives, various metal complexes represented by metal or rare earth complexes of 8-quinolinol derivatives, and polymeric compounds such as polythiophene, polyphenylene and polyphenylenevinylene. Although the luminescent layer has no particular restrictions as to the thickness, the suitable thickness thereof is generally from 1 nm to 5 $\mu$m, more preferably 5 nm to 1 $\mu$m, further preferably 10 nm to 500 nm.

As to the method of forming the luminescent layer, there is no particular restriction, but various methods including a resistance heating-utilized vapor deposition method, an electron-beam method, a sputtering method, a molecular lamination method, a coating method (e.g., a spin coating, cast coating or dip coating method) and an LB method can be adopted. Of these methods, resistance heating-utilized vapor deposition and coating methods are preferred over the others.

The materials for the hole injection layer and the hole transfer layer may be any materials so long as they have any one of the functions as an injector of the holes from the anode, a transferor of holes and a barrier against electrons injected from the cathode. Examples of a material having one of such functions include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, conductive polymers or oligomers, such as poly (N-vinylcarbazole) derivatives, aniline copolymers, thiophene oligomers and polythiophene, and the silane compounds of the present invention. The thickness of the hole injection layer and the hole transfer layer each, though it has no particular limitation, is generally from 1 nm to 5 $\mu$m, more preferably 5 nm to 1 $\mu$m, further preferably 10 nm to 500 nm. Each of the hole injection layer and the hole transfer layer may have a single-layer structure constituted of one or more of the materials described above or a multiple-layer structure made up of at least two layers having the same composition or different compositions.

As a method of forming a hole injection layer and a hole transfer layer, a vacuum evaporation method, an LB method, and a method of coating a compound capable of injecting or transferring holes in the form of a solution or dispersion in an appropriate solvent (using, e.g., a spin coating, cast coating or dip coating method) can be adopted. In the case of a coating method, the compound can be dissolved or dispersed in the presence of a resin component. Examples of a resin component usable therein include polyvinyl chloride, polycarbonate, polystyrene, polymethyl methacrylate, polybutyl methacrylate, polyester, polysulfone, polyphenylene oxide, polybutadiene, poly (N-vinylcarbazole), hydrocarbon resin, ketone resin, phenoxy resin, polyamide, ethyl cellulose, polyvinyl acetate, ABS resin, polyurethane, melamine resin, unsaturated polyester resin, alkyd resin, epoxy resin and silicone resin.

The materials for the electron injection layer and the electron transfer layer may be any materials so long as they have any one of the functions as an injector of the electrons from the cathode, a transferor of electrons and a barrier against holes injected from the anode. Examples of a compound having such a function include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodimide derivatives, fluorenylidenemethane derivatives, distyrylpyrazine derivatives, tetracarboxylic acid anhydrides of aromatic condensed rings such as naphthalene and perylene, phthalocyanine derivatives, various metal complexes represented by metal complexes of 8-quinolinol derivatives, metallophthalocyanine and metal complexes containing benzoxazole or benzothiazole ligands, and the silane compounds of the present invention. The suitable thickness of the electron injection layer and the electron transfer layer each, though it has no particular limitation, is generally from 1 nm to 5 μm, more preferably 5 nm to 1 μm, further preferably 10 nm to 500 nm. Each of the electron injection layer and the electron transfer layer may have a single-layer structure constituted of one or more of the compounds as described above, or a multiple-layer structure made up of at least two layers having the same composition or different compositions.

As a method of forming the electron injection layer and the electron transfer layer, a vacuum evaporation method, an LB method and a method of coating the compound(s) capable of injecting or transferring electrons in the form of a solution or dispersion in an appropriate solvent (using, e.g., a spin coating, cast coating or dip coating method) can be adopted In a case of adopting the coating method, the electron-injecting or transferring compounds can be dissolved or dispersed in the presence of a resin component. Examples of a resin component usable therein include the same resins as employed for the hole injection and transfer layers.

The materials for a protective layer may be any substances so long as they have a function capable of inhibiting the invasion of a device deterioration promoter, such as moisture or oxygen, into the device. Examples of such a substance include metals, such as In, Sn, Pb, Au, Cu, Ag, Al, Ti and Ni; metal oxides, such as MgO, SiO, $SiO_2$, $Al_2O_3$, GeO, NiO, CaO, BaO, $Fe_2O_3$, $Y_2O_3$ and $TiO_2$; metal fluorides, such as $MgF_2$, LiF, $AlF_3$ and $CaF_2$; polyethylene, polypropylene, polymethyl methacrylate, polyimide, polyurea, polytetrafluoroethylene, polychlorotrifluoroethylene, polydichlorodifluoroethylene, copolymer of chlorotrifluoroethylene and dichlorodifluoroethylene, copolymers prepared by polymerizing a mixture of tetrafluoroethylene and at least one comonomer, and fluorine-containing copolymers having cyclic structures in the main chain; a water-absorbing substance having a water absorption rate of at least 1%; and a moistureproof substance having a water absorption rate of at most 0.1%.

The protective layer also has no particular restriction as to the formation method, but any of a vacuum evaporation method, a sputtering method, a reactive sputtering method, a molecular beam epitaxy (MBE) method, a cluster ion beam method, an ion plating method, a plasma polymerization method (high frequency excitation ion plating method), a plasma chemical vapor deposition (CVD) method, a laser CVD method, a heat CVD method, a gas source CVD method and a coating method can be adopted for the formation thereof.

The present invention will now be illustrated in more detail by reference to the following examples. However, the invention should not be construed as being limited to these examples.

Synthesis of Compound (1—1)

To a solution containing 2.0 g of bis(4-bromophenyl)-diphenylsilane and 2.2 g of N,N'-diphenyl-4-vinylaniline in 50 ml of dimethylformamide, 2.63 g of tetrabutylammonium bromide, 3.38 g of potassium carbonate and 0.04 g of palladium acetate were added and stirred for 4 hours at 100° C. The reaction mixture was diluted with 200 ml of ethyl acetate and 200 ml of 1N hydrochloric acid aqueous solution, and the thus separated organic layer was washed with successive 200 ml of 1N hydrochloric acid aqueous solution, 200 ml of water, and 100 ml of saturated brine. The resulting solution was dried with sodium sulfate, and filtered. The filtrate obtained was concentrated to yield yellow oil. The yellow oil was purified by column chromatography (developing solvent: hexane/ethyl acetate mixture→chloroform) to yield 1.5 g of yellow solid (Compound (1—1)). The evaporated film of this yellow solid was found to have its λmax at 465 nm by the fluorescence spectrum measurement.

Reaction Scheme of Compound (1—1) Synthesis

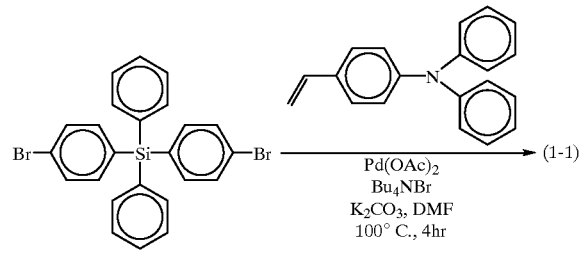

Comparative Example 1

A cleaned ITO substrate was placed in a vacuum evaporator, and onto this substrate a N,N'-diphenyl-N,N'-di(m-tolyl)benzidine (TPD) was evaporated to form a film having a thickness of 40 nm first, and then a tris(8-hydroxyquinolinato)aluminum complex (Alq) was evaporated thereonto to form a film having a thickness of 60 nm. Then, a patterned mask (for adjusting each emission area to 5 mm×5 mm) was set on the organic thin evaporated film, and further thereon, inside the vacuum evaporator, Mg and Ag were deposited simultaneously in a Mg/Ag ratio of 10/1 to form a metallic film having a thickness of 50 nm, followed by deposition of a 50 nm-thick Ag film.

The thus produced electroluminescent (EL) device was made to luminesce by applying thereto a DC constant voltage by means of a source measure unit, Model 2400, made by Toyo Technica Co., Ltd. And the luminance and the wavelength of the luminescence which the EL device showed were measured using a luminometer BM-8, made by Topcon Co., and a spectrum analyzer PMA-11, made by Hamamatsu Photonics Co., respectively. As a result of these measurements, the luminescence which the EL device gave off was found to be green luminescence having the $EL_{max}$ at 510 nm and the luminance of 3400 cd/m² under an operating voltage of 13 V. Thereafter, the EL device was allowed to stand for 2 days in an atmosphere of nitrogen, and made to luminesce again. On the luminous surface of the device, many dark spots were found out by visual observation.

Example 1

An EL device was produced in the same manner as in Comparative Example 1, except that the Compound (1—1) of the present invention was used in place of TPD, and evaluated by the same method as in Comparative Example 1. As a result, the device exhibited luminescence having the $EL_{max}$ at 510 nm and the luminance of 4680 cd/m² under an operating voltage of 13 V. Thereafter, the EL device was allowed to stand for 2 days in an atmosphere of nitrogen, and made to luminesce again. No dark spot was detected on the luminous surface of the device by visual observation.

Example 2

A cleaned ITO substrate was placed in a vacuum evaporator, and onto this substrate a Compound (1—1) was evaporated to form a film having a thickness of 40 nm, then a 3-(4-t-butylphenyl)-4-phenyl-5-biphenyl-1,2,4-triazole (TAZ) was evaporated thereon to to form a film having a thickness of 10 nm, and further a tris (8-hydroxyquinolinato) aluminium complex (Alq) was evaporated onto the TAZ film to form a film having a thickness of 50 nm. Furthermore, the cathode was deposited in the same manner as in Comparative Example 1. The thus produced device was evaluated by the same method as in Comparative Example 1. As a result, the device was found to give off blue luminescence having the $EL_{max}$ at 470 nm and the luminance of 1220 cd/m² under an operating voltage of 8 V.

In the same manner as the above, EL devices were produced using the other arylsilane compounds according to the present invention respectively, and they each were examined by the same method as mentioned above. As a result, it was confirmed that the compounds of the present invention functioned as EL device materials (charge transfer materials or luminescent materials). Further, it was found that the EL devices comprising the compounds of the present invention generated less dark spots and caused less short-circuits, namely they had excellent durability.

The arylsilane compounds of the present invention are usable as materials for organic EL devices, and the devices comprising the compounds of the present invention can have excellent electroluminescent characteristics, including color hue, luminance and durability. Further, the compounds of the present invention are utilizable for medical supplies, brightening agents, photographic materials, TV absorbing materials, laser dyes, color filter dyes and color conversion filters.

While the invention has been described in detail and with reference to specific embodiments thereof, it will be apparent to one skilled in the art that various changes and modifications can be made therein without departing from the spirit and scope thereof.

What is claimed is:

1. A compound represented by the following formula (1):

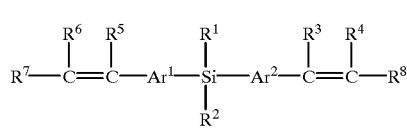

(1)

wherein each of $R^1$ and $R^2$ groups represents an aryl group containing no alkenyl substituent, or a heteroaryl group containing no alkenyl substituent; each of $R^3$, $R^4$, $R^5$ and $R^6$ groups represents a hydrogen atom or a substituent group; each of $R^7$ and $R^8$ groups represents an aryl group or a heteroaryl group; and each of $Ar^1$ and $Ar^2$ groups represents an arylene group or a heteroarylene group; provided that the compound represented by the formula (1) takes neither polymeric nor oligomeric form and the case is excluded therefrom wherein all or three of $R^1$, $R^2$, $Ar^1$ and $Ar^2$ groups have heteroaryl structures.

2. A luminescent device material, comprising a compound represented by the following formula (1):

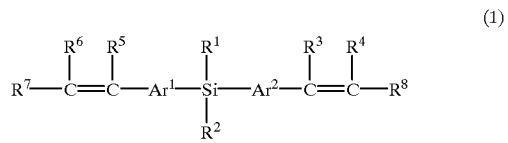

(1)

wherein each of $R^1$ and $R^2$ groups represents an aryl group containing no alkenyl substituent, or a heteroaryl group containing no alkenyl substituent; each of $R^3$, $R^4$, $R^5$ and $R^6$ groups represents a hydrogen atom or a substituent group; each of $R^7$ and $R^8$ groups represents an aryl group or a heteroaryl group; and each of $Ar^1$ and $Ar^2$ groups represents an arylene group or a heteroarylene group; provided that the compound represented by the formula (1) takes neither polymeric nor oligomeric form and the case is excluded therefrom wherein all or three of $R^1$, $R^2$, $Ar^1$ and $Ar^2$ groups have heteroaryl structures.

3. A luminescent device, containing at least one compound represented by the following formula (1):

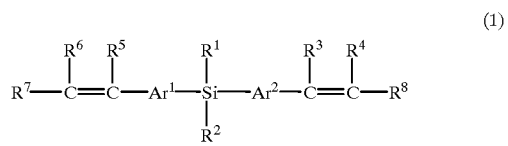

(1)

wherein each of $R^1$ and $R^2$ groups represents an aryl group containing no alkenyl substituent, or a heteroaryl group containing no alkenyl substituent; each of $R^3$, $R^4$, $R^5$ and $R^6$ groups represents a hydrogen atom or a substituent group; each of $R^7$ and $R^8$ groups represents an aryl group or a heteroaryl group; and each of $Ar^1$ and $Ar^2$ groups represents an arylene group or a heteroarylene group; provided that the compound represented by the formula (1) takes neither polymeric nor oligomeric form and the case is excluded therefrom wherein all or three of $R^1$, $R^2$, $Ar^1$ and $Ar^2$ groups have heteroaryl structures.

4. A method of synthesizing a compound represented by the following formula (1), comprising a step of reacting an alkenyl compound with the halide or trifluoromethanesulfonate derivative in the presence of a palladium catalyst to form the C—C bond:

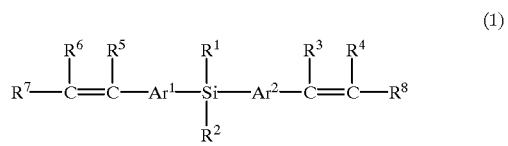

(1)

wherein each of $R^1$ and $R^2$ groups represents an aryl group containing no alkenyl substituent, or a heteroaryl group containing no alkenyl substituent; each of $R^3$, $R^4$, $R^5$ and $R^6$ groups represents a hydrogen atom or a substituent group; each of $R^7$ and $R^8$ groups represents an aryl group or a heteroaryl group; and each of $Ar^1$ and $Ar^2$ groups represents an arylene group or a heteroarylene group; provided that the compound represented by the formula (1) takes neither polymeric nor oligomeric form and the case is excluded therefrom wherein all or three of $R^1$, $R^2$, $Ar^1$ and $Ar^2$ groups have heteroaryl structures.

* * * * *